(12) United States Patent
Jasra et al.

(10) Patent No.: US 7,132,582 B2
(45) Date of Patent: Nov. 7, 2006

(54) CATALYTIC PROCESS FOR THE PREPARATION OF ISOLONGIFOLENE

(75) Inventors: Raksh Vir Jasra, Gujarat (IN); Beena Tyagi, Gujarat (IN); Manish Kumar Mishra, Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 487 days.

(21) Appl. No.: 10/448,457

(22) Filed: May 30, 2003

(65) Prior Publication Data

US 2004/0242936 A1     Dec. 2, 2004

(51) Int. Cl.
*C07C 5/23* (2006.01)
*B01J 20/34* (2006.01)
*C01G 25/02* (2006.01)

(52) U.S. Cl. .................. 585/668; 585/377; 585/664; 585/670; 502/29; 502/33; 502/349; 423/608

(58) Field of Classification Search ................ 585/377, 585/664, 668, 670; 502/29, 33, 349; 423/608
See application file for complete search history.

(56) References Cited

U.S. PATENT DOCUMENTS 3,718,698 A    2/1973  Hall .......................... 260/587
5,304,696 A *  4/1994  Khare et al. ................. 585/668
5,326,923 A *  7/1994  Cooper et al. ............... 585/725
6,420,305 B1 * 7/2002  Matsuzawa et al. ........ 502/222

FOREIGN PATENT DOCUMENTS

FR    2327975    5/1977

OTHER PUBLICATIONS

Database Caplus 'Online! Chemical Abstracts Service, Columbus, Ohio, US; Database Accession No. 2001:817301, XP002275587 & Xu Jingshi: "Study on Isomerisation of Longifolene Catalysed by TiO2/S2O8 2-" Huaxue Tongbao, No. 10, 2001, pp. 647-650, XP009027951, p. 648.

* cited by examiner

*Primary Examiner*—Glenn Caldarola
*Assistant Examiner*—In Suk Bullock
(74) *Attorney, Agent, or Firm*—Nixon & Vanderhye P.C.

(57) ABSTRACT

The present invention relates to a catalytic process for preparation of isolongifolene using nanocrystalline solid super acid. This process is an eco-friendly, single step, solvent free catalytic process for the preparation of a tricyclic sesqui-terpene hydrocarbon, isolongifolene. More particularly, the present invention provides a process for the catalytic isomerisation of longifolene to iso-longifolene using nano-crystalline sulfated zirconia as a solid super acid catalyst.

20 Claims, No Drawings

CATALYTIC PROCESS FOR THE PREPARATION OF ISOLONGIFOLENE

FIELD OF THE INVENTION

The present invention relates to a catalytic process for preparation of isolongifolene using nanocrystalline solid super acid. This process is an eco-friendly, single step, solvent free catalytic process for the preparation of a tricyclic sesqui-terpene hydrocarbon, isolongifolene.

More particularly, the present invention provides a process for the catalytic isomerisation of longifolene to isolongifolene using nano-crystalline sulfated zirconia as a solid super acid catalyst.

BACKGROUND OF THE INVENTION

Longifolene, $C_{15}H_{24}$ (decahydro-4,8,8-trimethyl-9-methylene-1-4-methanoazulene), is present in the Indian turpentine oil obtained from Chirpine (*Pinus longifolia*) to the extent of 5–7%. This is the largest tonnage sesquiterpene hydrocarbon available anywhere in the world.

The economical utilization of this terpene hydrocarbon involves its transformation into isomeric product iso-longifolene and its derivatives, which have extensively used in perfumery industry due to their woody and floral odor. The acid catalysed and hydroformylated products of this isomerized iso-longifolene (2,2,7,7-tetramethyltricyclo undec-5-ene) have also woody amber odor and are used as a flavor in many pharmaceutical industries.

This isomerized aromatic compound is of commercial importance in pharmaceutical industries as a flavor. Presently, iso-longifolene, $C_{15}H_{24}$, is mainly produced by a rearrangement of longifolene involving a number of steps catalysed by mineral acids like sulfuric acid/acetic acid. Currently used processes using mineral acids is a multi-step process which results into a large quantity of unwanted-waste chemicals as by-products that requires further treatment before disposal.

The use of hazardous mineral acid is not safe from handling point of view, as they are corrosive, irritant and also required in more than stoichiometric amount. Furthermore, isomerized product obtained using mineral acid possesses some colour due to impurities generated, which needs further purification.

Therefore, research efforts to prepare iso-longifolene from longifolene to overcome the above-mentioned disadvantages and to find an eco-friendly and safer catalyst are needed.

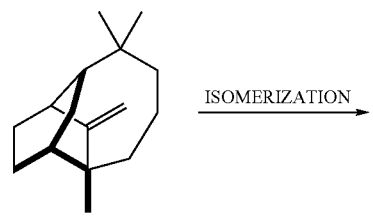

LONGIFOLENE.

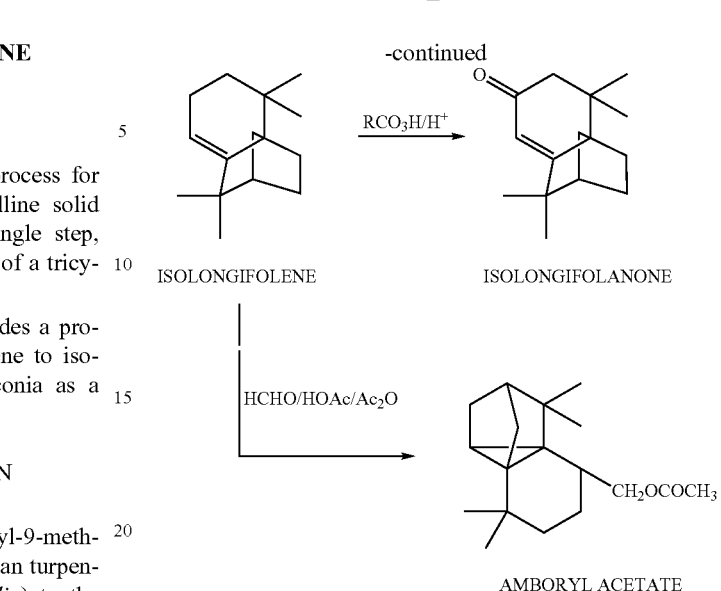

Reference is made to Sobti, R R and Dev, S. (Tetrahedron, Volume 26, 649, 1970) who have reported synthesis of isolongifolene from camphene-1-carboxylic acid using multi-step process. Besides involving many steps, this route has a drawback in producing a by-product $C_{13}$-keto acid, which is produced due to degradation of isolongifolene and uses reagents in stoichiometric amounts.

Prablad, J. R. et al. (Tetrahedron Letters, Volume 60, 417, 1964), who have reported the synthesis of isolongifolene from acid catalysed hydration of longifolene using acid treated silica gel. This synthesis strategy has a major drawback in the stability of the catalysts used as leaching of acid occurs from silica gel with prolonged use.

Beyler, R. E. and Ourisson, G. (J. Org. Chem. Volume 30, 2838, 1965) who have reported the synthesis of isolongifolene by treating longifolene with boron trifluoride etherate. In a typical reaction, longifolene is taken in sodium-dried ether to which boron trifluoride etherate is added and the mixture is refluxed on a steam bath for 60 minutes. Resultant dark brown mixture is added cautiously to excess of potassium hydroxide and ice. The mixture is stirred at ambient temperature for 90 minutes at the end of which the ether phase becomes straw yellow in colour. Separation and further extraction, water wash and, evaporation of ether result into light yellow isolongifolene. This route has drawback of using multi step synthesis of isolongifolene using hazardous chemicals like KOH, $BF_3$ and sodium metal. Separation of the product from the reaction mixture imbibes several chemical treatments and is additionally time consuming before product can be obtained.

Bisarya S. C. et al. (Tetrahedron Letters Volume 28, 2323, 1969) reports the synthesis of isolongifolene by treating longifolene with amberlyst-15 (Rohm and Haas) or acid treated silica gel at 95° C. for 36 hours with 95% yield of isolongifolene. This process has drawback in using amberlyst, ion exchange resin, which have poor thermal stability and also swell with prolonged use. Furthermore, the process takes 36 hours for completion.

Ramesha A. R. et al. (Organic Preparation Procedure International, Volume 31, 227, 1999) have reported the isomerization of longifolene using montmorillonite clay K10 at 120° C. with 100% selectivity and more than 90% conversion. However, the process has drawback in using natural clays which have lot of impurities and difficult to reproduce with the requisite surface acidity. Furthermore, the thermal stability of the clays is low and these get deactivated with use and regeneration and re-usability of the clay catalyst is not known.

Kula J., and Masarweh A. (Flavour and Fragrance Journal, Volume 13, 277, 1998) have reported acid catalyzed rearrangement of longifolene to isolongifolene using bromoacetic acid. This process has drawback in using liquid bromoacetic acid for isomerization, which is not safe to handle. Moreover, the separation of the product from the reaction mixture is difficult.

Nayak, U. R. and Dev S. (Tetrahedron, 8, 42, 1960) have reported the preparation of isolongifolene by hydration of longifolene using acetic acid and sulphuric acid in dioxane. Alongwith isolongifolene, 3-sesquiterpene alcohols were also obtained as by-products. Typically, 200 g of longifolene in 500 mL acetic acid and 40 mL 50% sulphuric was stirred with 475 mL dioxane. The mixture was kept at 22–24° C. for 60 h followed by warming at 52° C. for 10 h and then poured into 600 mL water. The aqueous layer was treated with ammonium sulphates then extracted three times with 50 mL petroleum ether. The combined organic product was washed with water and dried to evaporate the solvent. This dried product has around 66% isolongifolene. The process has drawback of using many steps and large number of reagents, which are hazardous and toxic. This also has problem of disposal of spent reagent.

Wang, Hui, et. al., Jilin daxue Ziran Kexue Xuebao, 1, 88–90, 2001, (Chinese) wherein the isolation and identification of iso-longifolene alongwith other products from the volatile oil in the stems and leaves of panax ginseng have been reported. However, this is time-consuming process and it cannot meet the demand of large production, thereby necessitates the development of a synthetic route.

OBJECTS OF THE INVENTION

The main object of the present invention is to provide a catalytic process for the preparation of iso-longifolene, which obviates the drawbacks as detailed above.

Another object of the present invention is to prepare isolongifolene by the isomerization of longifolene.

Yet another object of the present invention is to provide a single step and solvent free process for the isomerisation of longifolene.

Yet another object of the present invention is to provide a process wherein nano-crystalline sulfated zirconia solid super acid is used as a catalyst.

Yet another object of the present invention is to provide a process wherein isomerisation of longifolene with high conversion (>90%) and 100% selectivity for iso-longifolene.

Yet another object of the present invention is to provide a process wherein isomerisation of longifolene with high conversion and selectivity for iso-longifolene at atmospheric pressure and moderate temperature may be achieved.

Yet another object of the present invention is to provide a process wherein isomerisation of longifolene is carried out catalytically with high atom utilization and low E-factor.

SUMMARY OF THE INVENTION

Accordingly, the present invention comprises of a catalytic process for the preparation of isolongifolene comprising
(i) hydrolyzing zirconium alkoxide and sulfating with sulfuric acid to obtain sulfated zirconia;
(ii) drying the sulfated zirconia followed by calcining the dried sulfated zirconia;
(iii) activating the dried and sulfated zirconia catalyst obtained in step (ii) above,
(iv) reacting longifolene with the activated catalyst obtained in step (iii) in a solvent free medium, while maintaining the reactant to catalyst ratio in the range of 2–10 weight percent to obtain an isomerised product;
(v) separating the isomerised product iso-longifolene from the reaction mixture;
(vi) washing the catalyst to remove adhering materials and
(vii) drying the catalyst at 110° C. for 2–4 h followed by air calcination at 550° C. for a period between 4–8 h.

In one embodiment of the invention, the hydrolysis and sulfation in step (i) above is carried out by one-step or two-step sol-gel technique and in a medium selected from the group consisting of acid, basic or neutral medium, and at ambient temperature.

In another embodiment of the invention the sulfated zirconia is dried at a temperature of 110° C. for 8–12 hours followed by calcination at 550 to 650° C. for 2–6 hours.

In another embodiment of the invention, the dried and sulfated zirconia catalyst is activated prior to reaction at a temperature in the range of 400–450° C. for 2–4 hours.

In another embodiment of the invention the reaction of longifolene is carried out while maintaining the temperature of the reaction in the range of 120 to 200° C. and at atmospheric pressure and for a period selected from 0.5 to 6 h.

In another embodiment of the invention, the separation of the isomerised product iso-longifolene is carried out by filtration.

In yet another embodiment of the invention, the catalyst is washed with ethyl acetate to remove the adherent materials.

In another embodiment of the invention, the catalyst comprises nano-crystalline sulfated zirconia having (i) crystallite size, (ii) BET surface area, (iii) pore volume and (iv) pore size in the range of 10–100 nm; 80–120 $m^2g^{-1}$; 0.08–0.2 $cm^3g^{-1}$ and 35–60 Å respectively with catalytic active predominantly tetragonal crystalline phase.

DETAILED DESCRIPTION OF THE INVENTION

Nano-crystallite zirconia having sulphates as chelating bidentate species on the surface is used for catalytic conversion at atmospheric pressure. The hydrolysis of zirconium alkoxide or zirconium salts can be carried out in acidic, basic or neutral medium. The sulfation of zirconia with sulfuric acid can be carried by sol-gel technique using one-step as well as two-step procedures at ambient temperature. The solid acid catalyst has sulfur in the range of 0.5 to 2.5 weight % after calcination of the catalyst at the temperature of 600° C. The ratio of the reactant to solid acid catalyst ratio can be varied in the range of 2 to 10 weight by percent.

The temperature for the catalytic conversion can be in the range of 120 to 200° C. and the time period can be in the range of 0.5 to 6 h. The reaction is preferably carried out in a solvent free condition and in a single step procedure.

In a typical procedure for the preparation of the catalyst, zirconium iso-propoxide is hydrolysed into $ZrO_2$ and sulfated with sulfuric acid to sulfated zirconia. The hydrolysis and sulfation was carried out simultaneously during one-step procedure. In two-step procedure hydrolysis was carried out in first step followed by sulfation in second step. The hydrolysis was carried out in basic and neutral medium. The sample in all the cases was dried overnight at 110° C. and then calcined at 550–650° C. for 2 to 6 h. The catalyst thus obtained was cooled at ambient temperature. Activation of these prepared catalysts was done at 450° C. for 4 h prior to catalytic studies.

Catalytic studies were done in a stirred tank reactor of 50 ml capacity having attached temperature controller, water circulator, magnetic stirrer and moisture trap. Typically, longifolene (2 g) was taken in a 50 ml capacity round bottom flask to which the activated catalyst (0.2 g) was added so as the ratio of longifolene/catalysts is in the range of 2 to 10. The activation of the catalysts was done at 450° C. for 4 h. The round bottom flask was fitted with a condenser through which constant temperature water was circulated. Moisture trap was attached at the end of the condenser. The contents of the flask were constantly stirred using a magnetic stirrer. The flask was kept in an oil bath whose temperature was slowly raised to desired reaction temperature in the range of 120 to 200° C. The content of the flask were analyzed at different time intervals ranging from 0.5 to 6 h by Gas Chromatography, HP model 6890, using capillary column HP-5. Percent conversion of longifolene was calculated using following equation Percent conversion=$[n_0-n_f/n_0] \times 100$ Where, $n_0$=Number of moles of longifolene introduced before reaction.

$n_f$=Number of moles of longifolene remaining in the reaction mixture after reaction.

Structural characterization of above synthesized catalysts was done by FT-IR spectroscopy and X-ray powder diffraction techniques. The crystallite size was determined from X-ray diffraction data. Textural characterization for surface area, pore volume and pore size was carried out by nitrogen adsorption at 77K.

In the present invention nano-crystalline sulfated zirconia based catalysts are developed for the single step isomerisation of longifolene to produce selectively iso-longifolene product. These catalysts evinced highest activity (>90% conversion with 100% selectivity) in a solvent free condition.

Sulfated zirconia possesses surface acidity in super acidity range (Hammett indicator <−12) due to binding of sulphate groups to $Zr^{+4}$ through oxygen atoms. During sol-gel method, the porosity generated in the solid is sufficiently high to facilitate diffusion of longifolene/isolongifolene molecules towards and away from active acid sites. Longifolene double bond generates carbonium ion on reaction with acid sites and rearranges for isolongifolene.

Inventive steps adopted with respect to prior art are (i) a novel synthetic route based on solid acid catalysts for the preparation of isolongifolene; (ii) synthesis of nano-crystalline sulfated zirconia by one-step and two-steps sol-gel technique, in acid, basic as well as neutral medium for catalytical activity for the isomerisation of longifolene to isolongifolene with very higher conversion (>90%) and selectivity (100%) for isomerised product, (iii) the synthesis of isolongifolene in a single step and solvent free medium, (iv) relatively moderate conditions of temperature at atmospheric pressure for synthesis of isolongifolene in a less than an hour which makes the process energy efficient, (v) high atom utilization of the process as no by-products are produced and catalysts can be easily separated and re-used.

The following examples are given by the way of illustrations and therefore should not be constructed to limit the scope of the present invention.

EXAMPLE-1

1.02 mL of conc. $H_2SO_4$, diluted with 6.4 mL of $H_2O$ was added drop-wise to 30% solution of $Zr(OC_3H_7)_4$ in propanol or zirconium salt like zirconium nitrate. The hydrolysed sol was continuously stirred by magnetic stirrer for 3 h. The formed gel was first dried at ambient temperature for 3 h and then at 110° C. for 12 h. The dried gel was powdered to 170 mesh and calcined at 600° C. for 2 h. The prepared sample had crystallite size of 13 nm as determined from X-ray diffraction. Sulfur loaded on the catalysts as measured by elemental analysis was 1.2 wt %. 2 g of longifolene was taken in two-necked round bottom flask, which was put in an oil bath equipped with temperature controller, magnetic stirrer, condenser and circulator. The temperature of the oil bath was then slowly raised to the desired one, i.e., to 120° C. 0.2 gm of catalyst, pre-activated 450° C. in muffle furnace for 2 h was added to the reactant. The sample were taken out periodically by means of syringe and analysed by gas chromatography using HP-5 column. The percent conversion of longifolene was 72 to 75% with 100% selectivity after 3 to 6 h.

EXAMPLE-2

2 g of longifolene was taken in two-necked round bottom flask, which was put in an oil bath equipped with temperature controller, magnetic stirrer, condenser and circulator. The temperature of the oil bath was then slowly raised to the desired one, i.e., 140° C. 0.2 gm of catalyst prepared as described in Example-1, pre-activated at 450° C. in muffle furnace for 2 h was added to the reactant. The sample was taken out after 6 h by means of syringe and analysed by gas chromatography using HP-5 column. The percent conversion of longifolene was 85% with 100% selectivity after 6 h.

EXAMPLE-3

2 g of longifolene was taken in two-necked round bottom flask, which was put in an oil bath equipped with temperature controller, magnetic stirrer, condenser and circulator. The temperature of the oil bath was then slowly raised to the desired one, i.e., 160° C. 0.2 gm of catalyst prepared as described in Example-1, pre-activated at 450° C. in muffle furnace for 2 h was added to the reactant. The sample was periodically taken out after 2 to 6 h by means of syringe and analysed by gas chromatography using HP-5 column. The percent conversion of longifolene was 84 to 86% with 100% selectivity after 2 to 6 h.

EXAMPLE-4

2 g of longifolene was taken in two-necked round bottom flask, which was put in an oil bath equipped with temperature controller, magnetic stirrer, condenser and circulator. The temperature of the oil bath was then slowly raised to the desired one, i.e., 180° C. 0.2 gm of catalyst prepared as described in Example-1, pre-activated at 450° C. in muffle furnace for 2 h was added to the reactant. The sample was periodically taken out from 0.5 to 6 h by means of syringe and analysed by gas chromatography using HP-5 column. The percent conversion of longifolene was 91 to 92% with 100% selectivity after 0.5 to 6 h.

EXAMPLE-5

2 g of longifolene was taken in two-necked round bottom flask, which was put in an oil bath equipped with temperature controller, magnetic stirrer, condenser and circulator. The temperature of the oil bath was then slowly raised to the desired one, i.e., 190° C. 0.2 gm of catalyst prepared as described in Example-1, pre-activated at 450° C. in muffle furnace for 2 h was added to the reactant. The sample was periodically taken out after 0.5 to 4 h by means of syringe and analysed by gas chromatography using HP-5 column. The percent conversion of longifolene was 90 to 92% with 100% selectivity 0.5 to 4 h.

EXAMPLE-6

2 g of longifolene was taken in two-necked round bottom flask, which was put in an oil bath equipped with temperature controller, magnetic stirrer, condenser and circulator. The temperature of the oil bath was then slowly raised to the desired one, i.e., 200° C. 0.2 gm of catalyst prepared as described in Example-1, pre-activated at 450° C. in muffle furnace for 2 h was added to the reactant. The sample was periodically taken out after 0.5 to 4 h by means of syringe and analysed by gas chromatography using HP-5 column. The percent conversion of longifolene was 91 to 92% with 100% selectivity after 1 to 4 h.

EXAMPLE-7

1.02 mL of conc. $H_2SO_4$, was added to 30% solution of $Zr(OC_3H7)_4$ in propanol and then 6.4 mL of $H_2O$ was added drop-wise to this solution. The hydrolysed sol was continuously stirred by magnetic stirrer. The gel was immediately solidified. The formed gel was first dried at room temperature for 3 h and then at 110° C. for 12 h. The dried gel was powdered to 170 mesh and calcined at 600° C. for 2 h. The prepared sample had crystallite size of 11 nm as determined from X-ray diffraction. Sulfur loaded on the catalysts as measured by elemental analysis was 1.6 wt %. 2 g of longifolene was taken in two-necked round bottom flask, which was put in an oil bath equipped with temperature controller, magnetic stirrer, condenser and circulator. The temperature of the oil bath was then slowly raised to the desired one, i.e., to 140° C. 0.2 gm of the catalyst, pre-activated at 450° C. in muffle furnace for 2 h was added to the reactant. The sample were periodically taken out by means of syringe and analysed by gas chromatography using HP-5 column. The percent conversion of longifolene was 92% with 100% selectivity after 2 h.

EXAMPLE-8

2 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.2 gm of the catalyst prepared as described in Example-7 pre-activated at 450° C. in muffle furnace for 2 h was added to the reactant. The sample were periodically taken out by means of syringe and analysed by gas chromatography using HP-5 column. The percent conversion of longifolene was 93% with 85% selectivity after 2 h.

EXAMPLE-9

2 g of longifolene was taken in two-necked round bottom flask, which was put in an oil bath equipped with temperature controller, magnetic stirrer, condenser and circulator. The temperature of the oil bath was then slowly raised to the desired one, i.e., to 200° C. 0.2 gm of the catalyst prepared as described in Example-7, pre-activated at 450° C. in muffle furnace for 2 h was added to the reactant. The sample were periodically taken out by means of syringe and analysed by gas chromatography using HP-5 column. The percent conversion of longifolene was 93% with 80% selectivity after 2 h.

EXAMPLE-10

Aqueous ammonia (25%) was added drop-wise to 30% solution of $Zr(OC_3H7)_4$ in propanol until the pH of the mixture becomes 9–10. The hydrolysed sol was continuously stirred by magnetic stirrer for 3 h. The formed gel was first dried at room temperature for 3 h and then at 110° C. for 12 h. The dried gel was powdered to 170 mesh and stirred with 1N $H_2SO_4$(15 mL/g) for 30 min. After filtration, it was first dried at room temperature for 3 h and then at 110° C. for 12 h. The dried gel was powdered to 170 mesh and calcined at 600° C. for 2 h. The prepared sample had crystallite size of 11 nm as determined from X-ray diffraction. Sulfur loaded on the catalysts as measured by elemental analysis was 1.4 wt % 2 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.2 gm of catalyst, pre-activated at 450° C. in muffle furnace for 2 h was added to the reactant. The sample were taken out by means of syringe and analysed by gas chromatography using HP-5 column. The percent conversion of longifolene was 90% with 100% selectivity after 2 h.

EXAMPLE-11

2 g of longifolene was taken in two-necked round bottom flask, which was put in an oil bath equipped with temperature controller, magnetic stirrer, condenser and circulator. The temperature of the oil bath was then slowly raised to the desired one, i.e., to 200° C. 0.2 gm of catalyst prepared as described in Example-10, pre-activated at 450° C. in muffle furnace for 2 h was added to the reactant. The sample were taken out by means of syringe and analysed by gas chromatography using HP-5 column. The percent conversion of longifolene was 90% with 100% selectivity after 2 h.

EXAMPLE-12

6.4 mL of $H_2O$ was added drop-wise to 30% solution of $Zr(OC_3H7)_4$ in propanol. The hydrolysed sol was continuously stirred by magnetic stirrer for 3 h. The formed gel was first dried at room temperature for 3 h and then at 110 C for 12 h. The dried gel was powdered to 170 mesh and stirred with of 1N $H_2SO_4$(15 mL/g) for 30 min. After filtration, it was first dried at room temperature for 3 h and then at 110° C. for 12 h. The dried gel was powdered to 170 mesh and calcined at 600° C. for 2 h. The prepared sample had crystallite size of 100 nm as determined from X-ray diffraction. Sulfur loaded on the catalysts as measured by elemental analysis was 1.3 wt %. 2 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.2 gm of catalyst, pre-activated at 450° C. in muffle furnace for 2 h was added to the reactant. The sample were taken out by means of syringe and analysed by gas chromatography using HP-5 column. The percent conversion of longifolene was 92% with 100% selectivity after 2 h.

EXAMPLE-13

2 g of longifolene was taken in two-necked round bottom flask, which was put in an oil bath equipped with temperature controller, magnetic stirrer condenser and circulator. The temperature of the oil bath was then slowly raised to the desired one, i.e., to 200° C. 0.2 gm of catalyst prepared as described in Example-12, pre-activated at 450° C. in muffle furnace for 2 h was added to the reactant taken in the flask. The sample were taken out by means of syringe and analysed by gas chromatography using HP-5 column. The percent conversion of longifolene was 92% with 100% selectivity after 2 h.

EXAMPLE-14

The catalyst, prepared as described in Example-1, after the completion of the reaction as described in Example-4 was separated from the reaction mixture by filtration and washed with 10 mL of ethyl acetate solution at ambient temperature. Catalyst was dried in oven at 110° C. for 2–4 h followed by air calcination in muffle furnace at 550° C. for 4–8 h. The catalyst was cooled to ambient temperature) and labelled as Ex. 1-recycle. 1 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.1 gm of catalyst, Ex. 1-recycle was added to the reactant taken in the flask. The sample were taken out by means of syringe and analysed by gas chromatography using HP-5 column. The percent conversion of longifolene was 36% with 100% selectivity after 2 h.

EXAMPLE-15

The catalyst, prepared as described in Example-7, after the completion of the reaction as described in Example-8 was separated from the reaction mixture by filtration and washed with 10 mL of ethyl acetate solution at ambient temperature. Catalyst was dried in oven at 110° C. for 2–4 h followed by air calcination in muffle furnace at 550° C. for 4–8 h. The catalyst was cooled to ambient temperature) and labelled as Ex. 2-recycle. 1 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.1 gm of catalyst, Ex. 7-recycle was added to the reactant taken in the flask. The sample were taken out by means of syringe and analyzed by gas chromatography using HP-5 column. The percent conversion of longifolene was 90% with 100% selectivity after 2 h.

EXAMPLE-16

The catalyst, prepared as described in Example-10, after the completion of the reaction as described in Example-10 was separated from the reaction mixture by filtration and washed with 10 mL of ethyl acetate solution at ambient temperature. Catalyst was dried in oven at 110° C. for 2–4 h followed by air calcination in muffle furnace at 550° C. for 4–8 h. The catalyst was cooled to ambient temperature) and labelled as Ex. 10-recycle. 1 g of longifolene was taken in two-necked round bottom flask, which was put in an oil bath equipped with temperature controller, magnetic stirrer, condenser and circulator. The temperature of the oil bath was then slowly raised to the desired one, i.e., to 180° C. 0.1 gm of catalyst, Ex. 10-recycle was added to the reactant taken in the flask. The sample were taken out by means of syringe and analyzed by gas chromatography using HP-5 column. The percent conversion of longifolene was 90% with 100% selectivity after 2 h.

EXAMPLE-17

The catalyst, prepared as described in Example-12, after the completion of the reaction as described in Example-12 was separated from the reaction mixture by filtration and washed with 10 mL of ethyl acetate solution at ambient temperature. Catalyst was dried in oven at 110° C. for 2–4 h followed by air calcination in muffle furnace at 550° C. for 4–8 h. The catalysts was cooled to ambient temperature) and labelled as Ex. 12-recycle. 1 g of longifolene was taken in two-necked round bottom flask, which was put in an oil bath equipped with temperature controller, magnetic stirrer, condenser and circulator. The temperature of the oil bath was then slowly raised to the desired one, i.e, to 180° C. 0.1 gm of catalyst, Ex. 12-recycle was added to the reactant taken in the flask. The sample were taken out by means of syringe and analyzed by gas chromatography using HP-5 column. The percent conversion of longifolene was 91% with 100% selectivity after 2 h.

The main advantages of this process over conventional process include:
1. The present process employs solid acid catalyst, which are environment friendly, safe in handling and do not generate any waste or by-product.
2. The reaction process is a single step process without use of any solvent.
3. Furthermore, this process is carried at moderate conditions of pressure and temperature.
4. Catalysts being solid in nature can be easily separated from the liquid reaction mixture by means of filtration or centrifugation.
5. Catalysts being highly crystalline and thermally stable can be regenerated by thermal treatment and can be re-used.
6. Sulfated zirconia based solid acid catalysts are easy in transforming, handling etc. in comparison to conventional catalysts like $H_2SO_4$, $CH_3COOH$, and $BF_3.OEt_2$.

We claim:
1. A catalytic process for the preparation of isolongifolene comprising:
    (i) hydrolyzing zirconium alkoxide and sulfating with sulfuric acid to obtain sulfated zirconia;
    (ii) drying the sulfated zirconia followed by calcining the dried sulfated zirconia to obtain nano-crystalline sulfated zirconia catalyst;
    (iii) activating the dried and sulfated zirconia catalyst obtained in step (ii) above;
    (iv) reacting longifolene with the activated catalyst obtained in step (iii) in a solvent free medium, while maintaining the reactant to catalyst ratio in the range of 2–10 weight percent to obtain an isomerised product;

(v) separating the isomerised product iso longifolene from the reaction mixture;

(vi) washing the catalyst to remove adhering materials and (vii) drying the catalyst at 110° C. for 2–4 hours followed by air calcination at 550° C. for a period between 4–8 hours.

2. A process as claimed in claim 1 wherein the hydrolysis and sulfation in step (i) above is carried out by one-step or two-step sol-gel technique and in a medium selected from the group consisting of acid, basic or neutral medium, and at ambient temperature.

3. A process as claimed in claim 1 wherein the sulfated zirconia is dried at a temperature of 110° C. for 8–12 hours followed by calcination at 550 to 650° C. for 2–6 hours.

4. A process as claimed in claim 1 wherein the dried and sulfated zirconia catalyst is activated prior to reaction at a temperature in the range of 400–450° C. for 2–4 hours.

5. A process as claimed in claim 1 wherein the reaction of longifolene is carried out white maintaining the temperature of the reaction in the range of 120 to 200° C. and at atmospheric pressure and for a period selected from 0.5 to 6 hours.

6. A process as claimed in claim 1 wherein the separation of the isomerised product isolongifolene is carried out by filtration.

7. A process as claimed in claim 1 wherein the catalyst is washed with ethyl acetate to remove the adherent materials.

8. A process as claimed in claim 1 wherein the catalyst comprises nano-crystalline sulfated zirconia having (i) crystallite size; (ii) BET surface area; (iii) pore volume and (iv) pore size in the range of 10–100 nm; 80–120 $m^2g^{-1}$; 0.08–0.2 $cm^3g^{-1}$ and 35–60 Å respectively with catalytic active predominantly tetragonal crystalline phase.

9. A process as claimed in claim 1 wherein the isomerisation of longifolene is carried out in a single step without the use of any solvent.

10. A process as claimed in claim 1 wherein the nano-crystalline sulfated zirconia has a crystallite size is in the range of 10 to 100 nm.

11. A process as claimed in claim 1 wherein the nano-crystalline sulfated zirconia has a sulfur content in the range of 0.5 to 2.5 weight percent after calcination at 600° C.

12. A process as claimed in claim 1 wherein the BET surface area of nano-crystalline sulfated zirconia catalyst is maintained between 80 to 120 $m^2g^{-1}$.

13. A process as claimed in claim 1 wherein the isomerisation of longifolene is effected with greater than 90 percent conversion.

14. A process as claimed in claim 1 wherein selectivity for the isomerisation of longifolene is maintained between 98 to 100 percent.

15. A process as claimed in claim 1 wherein the isomerisation of longifolene is carried out with high atom utilization and low E-factor.

16. A process as claimed in claim 1 wherein the catalyst is separated and regenerated for recycling.

17. A catalytic process for the preparation of isolongifolene comprising:

(i) hydrolyzing zirconium alkoxide and sulfating with sulfuric acid to obtain sulfated zirconia by a sol-gel technique;

(ii) drying and calcining the sulfated zirconia to obtain nano-crystalline sulfated zirconia catalyst;

(iii) activating the nano-crystalline sulfated zirconia catalyst;

(iv) reacting longifolene with the activated nano-crystalline sulfated zirconia catalyst in a solvent free medium, while maintaining a ratio between reactant and catalyst in the range of 2 to 10 by weight percent to obtain isomerised product and (v) separating isolongifolene from reactant mixture.

18. A process as claimed in claim 17 wherein the nano-crystalline sulfated zirconia catalyst has (i) crystallite size; (ii) BET surface area; (iii) pore volume and (iv) pore size in the range of 10–100 nm; 80–120 $m^2g^{-1}$; 0.08–0.2 $cm^3g^{-1}$ and 35–60 Å respectively with catalytic active predominantly tetragonal crystalline phase.

19. A process as claimed in claim 17 wherein the isomerisation of longifolene is effected with greater than 90 percent conversion.

20. A process as claimed in claim 17 wherein selectivity for the isomerisation of longifolene is between 98 to 100 percent.

* * * * *